US005735902A

United States Patent [19]
Li et al.

[11] Patent Number: 5,735,902
[45] Date of Patent: *Apr. 7, 1998

[54] HAND IMPLANT DEVICE

[75] Inventors: Shu-Tung Li, Oakland, N.J.; Jack A. McCarthy, Omaha, Nebr.; William G. Rodkey, Edwards; J. Richard Steadman, Vail, both of Colo.

[73] Assignee: ReGen Biologics, Inc., Redwood City, Calif.

[*] Notice: The term of this patent shall not extend beyond the expiration date of Pat. No. 4,880,429.

[21] Appl. No.: 735,891

[22] Filed: Oct. 23, 1996

Related U.S. Application Data

[63] Continuation-in-part of Ser. No. 232,743, Apr. 25, 1994, Pat. No. 5,624,463, which is a continuation-in-part of Ser. No. 809,003, Dec. 17, 1991, Pat. No. 5,306,311, which is a continuation-in-part of Ser. No. 520,027, May 7, 1990, Pat. No. 5,108,438, which is a continuation-in-part of Ser. No. 317,951, Mar. 2, 1989, Pat. No. 5,007,934, which is a continuation-in-part of Ser. No. 75,352, Jul. 20, 1987, Pat. No. 5,880,429.

[51] Int. Cl.⁶ ............................................. A61F 2/32
[52] U.S. Cl. ............................................. 623/18
[58] Field of Search .......................... 623/11, 12, 16, 623/18, 17, 66

[56] References Cited

U.S. PATENT DOCUMENTS

| | | | |
|---|---|---|---|
| 3,443,261 | 5/1969 | Battista et al. | 3/1 |
| 3,551,560 | 12/1970 | Thiele | 424/95 |
| 3,855,638 | 12/1974 | Pilliar | 3/1 |
| 4,055,862 | 11/1977 | Farling | 3/1.91 |
| 4,060,081 | 11/1977 | Yannas et al. | 128/156 |
| 4,064,567 | 12/1977 | Burstein et al. | 3/1.9 |
| 4,280,954 | 7/1981 | Yannas et al. | 260/123.7 |
| 4,291,013 | 9/1981 | Wahlig et al. | 424/16 |
| 4,350,629 | 9/1982 | Yannas et al. | 260/123.7 |
| 4,385,404 | 5/1983 | Sully et al. | 3/1.91 |
| 4,400,833 | 8/1983 | Kurland | 3/1 |
| 4,418,691 | 12/1983 | Yannas et al. | 128/156 |
| 4,448,718 | 5/1984 | Yannas et al. | 260/123 |
| 4,458,678 | 7/1984 | Yannas et al. | 128/155 |
| 4,505,266 | 3/1985 | Yannas et al. | 128/1 R |
| 4,542,539 | 9/1985 | Rowe et al. | 623/16 |
| 4,544,516 | 10/1985 | Hughes et al. | 264/108 |
| 4,578,079 | 3/1986 | Ruoslahti et al. | 623/11 |
| 4,589,881 | 5/1986 | Pierschbacher et al. | 623/11 |
| 4,614,794 | 9/1986 | Easton et al. | 530/356 |
| 4,620,327 | 11/1986 | Caplan et al. | 632/10 |
| 4,627,853 | 12/1986 | Campbell et al. | 623/16 |
| 4,642,120 | 2/1987 | Nevo et al. | 623/16 |
| 4,787,900 | 11/1988 | Yannas | 623/1 |
| 4,801,299 | 1/1989 | Brendel et al. | 623/1 |
| 4,837,285 | 6/1989 | Berg et al. | 530/356 |
| 4,846,835 | 7/1989 | Grande | 623/11 |
| 4,880,429 | 11/1989 | Stone | 623/17 |
| 4,963,146 | 10/1990 | Li. | |
| 5,002,583 | 3/1991 | Pitaru et al. | 623/66 |
| 5,007,934 | 4/1991 | Stone | 623/20 |
| 5,026,381 | 6/1991 | Li et al. | 606/152 |
| 5,108,438 | 4/1992 | Stone | 623/17 |
| 5,116,374 | 5/1992 | Stone | 623/16 |
| 5,123,925 | 6/1992 | Smeslav et al. | 623/16 |
| 5,206,028 | 4/1993 | Li et al. | 424/484 |
| 5,263,984 | 11/1993 | Li et al. | 623/15 |
| 5,306,311 | 4/1994 | Stone et al. | 623/18 |

FOREIGN PATENT DOCUMENTS

| | | |
|---|---|---|
| 1170001 | 3/1984 | Canada. |
| 0277678 | 8/1988 | European Pat. Off.. |
| 0 349 173 | 1/1990 | European Pat. Off.. |
| 2 642 301 | 8/1990 | France. |
| 1515963 | 7/1976 | United Kingdom. |
| 8303536 | 10/1983 | WIPO. |
| 8910738 | 4/1989 | WIPO. |
| 90/12603 | 11/1990 | WIPO. |
| 91/16867 | 11/1991 | WIPO. |

OTHER PUBLICATIONS

Conolly et al., "Revision Procedures for Complications of Surgery for Osteoarthritis of the Carpometacarpal Joint of the Thumb", Journal of Hand Surgery (1993) 18B(4): 533–539.

Cooney et al., "Total Arthroplasty of the Thumb Trapeziometacarpal Joint", Clinical Orthopaedics and Related Research, (1987) 220: 35–45.

Kessler et al., "Proplast stabilized stemless trapezium implant", Journal of Hand Surgery, (1984) 9A(2): 227–231.

Kleinert et al., "Silicone Implants", Hand Clinics (1986) 2(2): 270–290.

Kvarnes et al., "Osteoarthritis of the Carpometacarpal Joint of the Thumb.", Journal of Hand Surgery, (1985) 10–B(2): 117–120.

Lucht et al., "Soft Tissue Interposition Arthroplasty for Osteoarthritis of the Carpometacarpal Joint of the Thumb", Acta orthop. scand. (1980) 51: 767–771.

Robinson et al., "Abductor pollicis longus tendon anthroplasty of the trapezio–metacarpal joint: Surgical technique and results", Journal of Hand Surgery, (1991) 16A(3): 504–509.

Sollerman et al., "Replacement of the OS Trapezium by Polyurethane Implants", Scand J Plast Reconstr Hand Surg (1993) 27: 217–221.

Sollerman et al., "Silastic Replacement of the Trapezuim for Arthrosis—A Twelve Year Follow–up Study" Journal of Hand Surgery (1988) 13B(4): 426–429.

(List continued on next page.)

*Primary Examiner*—David Isabella
*Attorney, Agent, or Firm*—Fish & Richardson P.C.

[57] ABSTRACT

A hand augmentation device to be used to replace diseased tissue of a hand bone. The device includes a dry matrix, which contains at least 75% by weight biocompatible and bioresorbable biopolymeric fibers such as collagen fibers or polysaccharide fibers, and has a height of 2 mm to 4 cm, a width of 0.5 cm to 6 cm, a depth of 0.5 cm to 6 cm, a density of 0.1 g/cm$^3$ to 0.5 g/cm$^3$, and a pore size of 50 μm to 300 μm.

20 Claims, No Drawings

OTHER PUBLICATIONS

Swanson et al., "Reconstruction of the Thumb Basal Joints", clinical Orthopaedics and Related Research (1987) 220: 68–85.

Watson et al., "Evolution of Arthritis of the Wrist", Clinical Orthopaedics and Related Research (1986) 202: 57–67.

Sengupta et al. (1974) *J. Bone Surg.*56B 1:167–177.

Rodrigo et al. (1978) *Clin. Orthop.*134:342–349.

Engkvist et al. (1979) *Scan. J. Plast. Reconstr. Surg.*13:361–369.

Yannas (1979) *Am. Chem.*16:1–9.

Gross (1980) *Oral Surgery*49:21–26.

Rubak (1982) *Acta Orthop. Scan.*53:181–186.

Nyilas et al. (1983) *Trans. Am. Soc. Artif. Intern. Organs.*29:307–312.

Arnoczky et al. (1985) *Arthroscopy*1:247.

Webber et al. (1985) *J. Ortho. Res.*3(1):36.

Petite and Rault (1990) *J. Biomed. Mat. Res.*24:179–187.

Rubash et al. ( ) *Clin. Orth. Rel. Res.*271:2–96.

HAND IMPLANT DEVICE

CROSS REFERENCE TO RELATED APPLICATIONS

This application is a continuation-in-part of U.S. patent application Ser. No.08/232,743, filed Apr. 25, 1994, now U.S. Pat. No. 5,624,423, which, in turn, is a continuation-in-part of U.S. patent application Ser. No. 07/809,003, filed Dec. 17, 1991, now U.S. Pat. No. 5,306,311, which, in turn, is a continuation-in-part application of U.S. Ser. No. 07/520,027, filed May 7, 1990, now U.S. Pat. No. 5,108,438, which, in turn, is a continuation-in-part application of U.S. Ser. No. 07/317,951, filed Mar. 2, 1989, now U.S. Pat. No. 5,007,934, which, in turn, is a continuation-in-part of U.S. Ser. No. 07/075,352, filed Jul. 20, 1987, now U.S. Pat. No. 4,880,429.

FIELD OF THE INVENTION

The present invention is in the field of implantable medical devices, and more particularly, is directed to devices useful as augmentation implants for tissue repair in the hand.

BACKGROUND OF THE INVENTION

The hand presents unique anatomic configurations and are exposed to a variety of biomechanical loads and demands. Consequently, there is a propensity for degenerative joint disease to occur in the hand both as progressive osteoarthritis as well as secondary to trauma. In addition to the basal joints of the thumb which are frequently observed in degenerative changes, numerous osteoarthroses and osteoarthritic changes occur in the carpal metacarpal joints, the head of the ulna, the metacarpal phalangeal joints, and the proximal interphalangeal joints of the fingers.

Treatment of injured or diseased osteoarthroses and osteoarthritic conditions of the hand has generally been by surgical repair, by excision and by using autografts, allografts, and artificial materials including metals and plastics. Some of these procedures include joint arthrodesis, arthroplasty with excision or resection of part or all of the effected bone, arthroplasty with interposition of autogenous tissue, allograft tissue, or a metal.

Alternatively, replacements have also been made with synthetic polymers such as silicone rubber, polyurethane, or Proplast (a silicone-polytetrafluroethylene or teflon composite).

Regardless of the various methods and techniques used, there appears to be a high degree of complications and outright failures. For example, arthrodesis involving fusing the articulating surfaces renders the joint stiff and unmovable. Many of the interpositional implants tend to dislodge or migrate. After many years of experience with the silicone implants, it is now recognized that silicone induced synovitis develops in the majority of patients and results in complete failure as a hand implant. Regardless of the procedure used, many of these patients continue to suffer pain, weakness, swelling and discomfort in the involved joint.

SUMMARY OF THE INVENTION

A feature of the present invention features a hand augmentation device to be used to replace a part or the entirety of a hand bone, i.e., one of the trapezium, trapezoid, scaphoid, lunate, capitate, hamate, triquetral, and pisiform bones. The device includes a dry matrix, which contains at least 75% (i.e., 75–100%) by weight biocompatible and bioresorbable (i.e., completely or partially; in any event, at least 10% bioresorbable) biopolymeric fibers such as collagen fibers (prepared from type I collagen or another type of collagen) or polysaccharide fibers, and has a height of 2 mm to 4 cm (preferably, 0.5 cm to 1.5 cm), a width of 0.5 cm to 6 cm (preferably, 1 cm to 2 cm), a depth of 0.5 cm to 6 cm (preferably, 1 cm to 2 cm), a density of 0.1 g/cm$^3$ to 0.5 g/cm$^3$ (preferably, 0.15 g/cm$^3$ to 0.3 g/cm$^3$), and a pore size of 50 µm to 300 µm (preferably, 100 µm to 200 µm). The dryness of the matrix of this invention can be easily achieved by air drying in a hood overnight, or by any other methods which bring about the same or similar state of dryness. The dimensions (i.e., height, width, depth, density, and pore size) of the matrix are determined in such a state of dryness. The pore size of the matrix is determined by scanning electron micrography (see below) or by any other analogous or suitable method. The matrix can be of any shape; however, a regular shape, such as a cylinder (e.g., a disk), a square bar, or a cone, is preferred.

If desired, the device can further include a bioactive substance (e.g., a glycosaminoglycan, growth factor, an antibiotic, a glycoprotein, or a combination thereof), up to 25% by weight and dispersed in the matrix. Examples of growth factors which can be dispersed in the matrix include, but are not limited to, bone morphogenetic protein, transforming growth factor β, fibroblast growth factor, epidermal growth factor, and insulin-like growth factor.

Another aspect of this invention features a method of fabricating a hand augmentation device as described above. The method includes the steps of obtaining biocompatible and bioresorbable biopolymeric fibers in an aqueous dispersion (to which a bioactive substance can be added, if desired); coacervating the dispersed fibers; molding the coacervated fibers; freeze-drying the molded fibers; and, molecularly crosslinking the dried fibers (e.g., either with a crosslinking agent such as glutaraldehyde, formaldehyde, carbodiimide, hexamethylene diisocyanate, polyglycerol polyglycidyl ether, or a combination thereof; or by a dehydrothermal process).

A further aspect of this invention features a method of using a hand augmentation device as described above. The method includes resecting diseased tissue from a hand bone (i.e., removing a part or the entirety of one of the trapezium, trapezoid, scaphoid, lunate, capitate, hamate, triquetral, and pisiform bones); forming an implant from the device to have a size and shape substantially those of the resected tissue; and securing the formed implant to the bone to replace the resected tissue (e.g., with sutures or pins).

Other features or advantages of the present invention will be apparent from the following detailed description and also from the appending claims.

DESCRIPTION OF THE INVENTION

It has been discovered that an augmentation implant fabricated from biocompatible and bioresorbable fibers can be surgically implanted into the hand so as to provide normal joint motion and strength. This augmentation implant also acts as a scaffold for tissue in growth based on its physical characteristics of the implant.

An exemplary hand implant device of this invention is a porous dry matrix which extends circumferentially or laterally at least in part about a central axis. In a preferred form, the augmentation implant has the shape of a disk which extends circumferentially about the axis and has a maximum height of approximately 3 cm and a maximum radial dimension of approximately 3 cm.

The hand implant device may be fabricated of any biocompatible, bioresorbable biopolymeric fibers which include a natural material or an analog thereof which can provide mechanical strength and protection and lubrication while encouraging tissue in growth (e.g., collagen, polysaccharide, elastin, fibrin or biosynthetic analogs thereof). In a preferred embodiment of this invention, collagen based material is used. If desired, a composite of collagen material and a bioactive substance, such as an antibiotic, may be used with collagen material making up at least 75% of the total dry weight of the device.

The matrix has a pore size no less than 50 µm for the ingrowth of tissue. In this regard, the matrix is functioning as a temporary scaffold. In order to maintain the necessary mechanical properties for implantation and in vivo function, the density of the matrix must be in the range of from 0.1 g/cm$^3$ to about 0.5 g/cm$^3$ for maintaining the shape of the implant in vivo.

The temporary stability of the shape of the structure when in vivo, and the rate of matrix resorption, are both attributed to the effective crosslinking formation between the fibers. The crosslinking reagents used may be any biocompatible bifunctional reagents which interacts with amino groups, carboxyl, or hydroxyl groups resulting in covalent bond formation between adjacent molecules. Useful crosslinking reagents include aldehyde, hexamethylene diisocyanate, bisimidate, polyglycerol polyglycidyl ether, and carbodiimide.

Intermolecular crosslinkages can also be established through a dehydrothermal process (heat and vacuum treatment) which results in peptide bond formation between an epsilon amino group of lysine or hydroxylysine and a carboxyl group of aspartic or glutamic acid.

The crosslinked device has a relatively high thermal stability between about 55°–85° C. for sufficient in vivo stability. This may be achieved through manipulation of the crosslinking conditions, including reagent concentration, temperature, pH, and time.

The crosslinked device maintains a sufficient degree of hydrophilicity and elasticity to sustain mechanical stress and to protect and lubricate the joint. In addition, the structure provides an ideal environment for cell infiltration and extracellular matrix synthesis and deposition resulting in regeneration of joint tissue.

In an embodiment of the invention, the hand augmentation implant device is constructed mainly of type I collagen fibers. Type I collagen fibers may be obtained from the Achilles tendons of animals. However, the fibers may also be obtained from animal skin or from the skin or tendon of humans. The tissues are treated with a series of mechanical and chemical means to either totally remove the non-collagenous materials or reduce them to a minimal level.

In the preferred processing steps, the tendon or skin is mechanically disintegrated into fine pieces useful for further processing. The disintegration may be achieved by grinding the tissue at liquid nitrogen temperature, or by cutting the tissue into small pieces with a sharp knife. In certain applications, the tendons are mechanically disintegrated along the fiber direction in order to maintain the length of the fibers for mechanical strength.

Salt (NaCl) extraction of tendon at neutral pH removes a small portion of the collagen molecules that are newly synthesized and have not yet been incorporated into the stable fibrils. Salt also removes some glycoproteins and proteoglycans that are associated with collagen through electrostatic interactions. Other salts such as KCl and the like can be used as a substitute for NaCl.

Lipids that are associated with the cell membranes or collagenous matrices may be removed by extracting with detergents such as Triton X-100, or by extracting with ether-ethanol mixtures or by a combination of detergent and ether-alcohol. The concentration of Triton X-100 is usually about 2–4%, but is preferably about 3%. The preferred mixture of ether-ethanol is usually at about a 1:1 ratio (v/v). The period of extraction is usually from 8 hours to 96 hours, preferably from about 24 to 48 hours.

Further extraction may be accomplished by matrix swelling conducted at two extreme pHs. Both acidic and basic swelling weakens the non-covalent intermolecular interactions, thus facilitating the release of non-covalently attached glycoproteins, glycosaminoglycans, and other non-collagenous molecules through the open pores of the collagenous matrices.

The swelling of matrix at alkaline pH is done by treating the collagen at high pH with $Ca(OH)_2$, NaOH, or the like, for a period of about 16–96 hours. Alkali extraction in the presence of triple-helical stabilizing salts such at $(CH_3)_4NCl$, $(NH_4)_2SO_4$, or the like reduces the potential risk of denaturation of the collagen. Alkali treatment dissociates the non-crosslinked glycoproteins and glycosaminoglycans from the collagen matrices. The alkali also removes the residual lipids through saponification.

The acid swelling may be conducted at a low pH in the presence of acetic acid, lactic acid, HCl, or the like. Like the alkali treatment, the acid swelling removes non-crosslinked glycoproteins and glycosaminoglycans.

The non-triple helical portions of the molecule (telopeptides) are involved in intermolecular crosslinking formation. They are weak antigens and are susceptible to attack by proteases, such as pepsin, trypsin, and the like. Prolonged digestion with such proteases dissociates the fibrils (fibers) into individual molecules. However, if the digestion process is properly controlled such that maximal telopeptides are removed without complete dissociation, the immunogenic properties of the fibrils can be reduced to a minimal level without compromising the mechanical strength. For example, to isolate molecular collagen, the digestion of skin or tendon with pepsin is usually conducted at an enzyme:collagen ratio of about 1:10 for about 24–96 hours at below room temperature. In comparison, fibrils may be obtained by limited pepsin digestion achieved at a ratio of about 1:100 (enzyme:collagen) for about 8–24 hours at 4° C.

Collagen fibers obtained according to this methodology are then used to fabricate the hand augmentation implant of the present invention. However, it must be appreciated that collagen obtained from other sources, such as biosynthetically-produced collagen or analogs thereof may also be used in the construction of the augmentation implant.

The method of fabrication includes molding the hydrated collagen fibers into a predetermined shape using a mold made of implantable stainless steel or biocompatible plastics such as teflon, polypropylene, delrin, or combination of these materials. For an example of such a mold and its use, see FIG. 5 of U.S. Pat. No. 5,306,311 and the accompanying text.

Without further elaboration, it is believed that a person of ordinary skill in the art can, based on the description herein, utilize the present invention to its fullest extent. The following specific embodiments are, therefore, to be construed as merely illustrative, and not limitative of the remainder of the disclosure in any way whatsoever. All publications cited herein are incorporated by reference.

Preparation of Purified Collagen

A. Source

Bovine, porcine, or ovine Achilles tendon is obtained from USDA-approved slaughter houses as the source for preparing type I collagen. The preferred age of the animals is between 12–18 months. The tissue is kept cold during the purification process except where specified to minimize bacteria contamination and tissue degradation.

B. Mechanical Disintegration

The adhering tissues of carefully selected tendons are first scrapped off mechanically. The tendons are then minced or cut into fine pieces and washed in excess quantities (10 volumes) of cold water to remove residual blood proteins and water soluble materials.

C. Salt Extraction

The washed tendons are extracted in ten volumes of 5% NaCl for 24 (±4) hours to remove salt soluble materials. The salt extracted tendons are repeatedly washed in about 10 volumes of water to remove the salt.

D. Lipid Extraction

The material is extracted in 3% Triton X-100 for 24 (±2) hours. The detergent is removed by extensive washing with water. The material is then extracted in 3–4 volumes of ether-ethanol (1:1 vol/vol) for 24 (±2) hours to further minimize the lipid content. The lipid extracted material is extensively washed in water to remove the ether and ethanol.

E. Matrix Swelling

The material is then subjected to two extreme pH extractions to remove non-collagenous materials. Alkaline extraction is conducted with 3–4 volumes of 0.5M NaOH at pH 12.5–13.5 at room temperature in the presence of 1.0M $Na_2SO_4$ for 24 (±2) hours with mild agitation.

Following alkaline extraction, the pH is neutralized with HCl and the material is washed with water. The pH is then adjusted to 2.5–3.0 by adding concentrated lactic acid to a final concentration of 0.5M. The acid extraction is continued for 24 (±2) hours with agitation.

F. Limited Proteolytic Digestion

The acid swollen tendon is then subjected to a limited proteolytic digestion with pepsin (enzyme:collagen=1:100) for 16 (±2) hours at 4° C. The pepsin and telopeptides are removed through dialysis.

The swollen fibrillar material is then coacervated by adjusting the pH to its isoionic point (between pH 4.5–5.0) with 1M NaOH or HCl. The aggregated collagen fibers are harvested by filtration, and the filtered material extensively washed with cold buffered solution. The highly purified type I collagen is freeze dried and then stored at room temperature until use.

Fabrication of a Hand Implant Device from Collagen Fibers

An aliquot of the purified collagen is first weighed and dispersed in 0.1M lactic acid, homogenized with a Silverson Homogenizer, filtered with a stainless steel mesh filter (40 mesh). The dispersion has a collagen content of 0.75% (w/v). Aliquots of the dispersed collagen fibers are coacervated by adding 0.3% $NH_4OH$ to its isoelectric point (pH 4.5–5.0).

The coacervated hydrated collagen fibers are carefully fit into a mold of specified dimensions in a manner similar to that described in Example 3 of U.S. Pat. No. 5,306,311. In particular, the fibers are partially dehydrated by applying force in the direction of the piston until the desirable dimension and density is obtained according to the design requirements.

The partially dehydrated fibers are frozen at −20° C., removed from the mold, and placed into a freeze dryer (virtis) and freeze dried first at −10° C. for 48 hours and then at 20° C. for an additional 16 hours.

The resulting freeze dried structure is crosslinked with vapor HCHO (generated from 2% HCHO solution at 25° C.) at 95% humidity for 24 hours.

The crosslinked implant device is extensively rinsed with distilled water, air dried for at least 8 hours or overnight under hood, and packaged for sterilization.

The pore size of the implant device can be controlled by varying the density of the matrix and by controlling the speed of freezing of the matrix prior to freeze drying, and is determined from scanning electron micrographs. A pore size is defined as the longest distance across an open pore.

Fabrication of a Hand Implant Device from Polysaccharide Fibers

Chitosan polysaccharide (Sigma Chemicals, St. Louis, Mo.) is dissolved in 1% acetic acid. The amount and acid solution used is such that a 1.5% of chitosan solution is reached. An aliquot of the chitosan solution is slowly neutralized by adding 0.01M NaOH to coacervate the chitosan fibers.

The coacervated hydrated fibers thus prepared are fit into the mold. The fibers are partially dehydrated to the desired dimension and density.

The partially dehydrated fibers are frozen at −20° C., turned out of the mold, and placed into a freeze dryer (Virtis) and freeze dried first at −10° C. for 48 hours and then at 20° C. for an additional 16 hours.

The resulting freeze dried structure is crosslinked with vapor HCHO (generated from 2% HCHO solution at 25° C.) at 95% humidity for 24 hours.

The crosslinked implant device is extensively rinsed with distilled water, air dried for at least 8 hours or overnight under hood, and packaged for sterilization. Its pore size is controlled and determined by the above-described methods used for fabricating the implant device from collagen fibers.

In Vivo Testing of an Hand Implant

Six New Zealand White rabbits weighing 3 to 4 kg were used in the study. One forelimb of each rabbit was operated upon. Each animal was taken to a sterile operating room after adequate anesthesia with an intramuscular injection of a combination of acepromazine, ketamine and xylazine. The left leg was shaved and prepped. An incision was then made over the dorsum of the carpus to expose the carpus.

The rabbits were divided into two groups. Group 1 included four rabbits which underwent total excision of the scaphoid, trapezium and trapezoid bones of the carpal metacarpal region in one forelimb. Following this excision, a collagen implant was used to fill the defect in each of the three animals. More specifically, an implant shaped from a disk-shaped collagen implant (height: 0.9 cm; radius: 1 cm; density: 0.2%; and pore size: 100 µm–300 µm) with a surgery scalpel was used to fill the defect in each animal. The implantation technique consisted of placing two size 4-0 nonabsorbable sutures through the volar capsule and then directly through the implant, and the sutures were tied over the top of the implant to stabilize it in place. The closure of the surgical wound was done routinely. The fourth animal in this group had the defect filled with autogenous flexor digitorum tendon, a procedure identical to that typically done in human patients. The two animals in Group 2 underwent complete excision of the scaphoid and lunate bones. In one of these two animals, the defect was filled with the collagen augmentation implant, and in the other, the defect was filled with autogenous flexor digitorum tendon. The animals in both groups were allowed weight-bearing without restriction following the surgery. There were no intraoperative or immediate post-operative complications.

The animals were carried out for six weeks following surgery prior to harvest of the operated limbs. Five of the six animals had remained stable with no complications. The one animal in Group 2 that had undergone a scapholunate excision with an autogenous tendon implant had luxated the carpal joint and the tendon implant had been displaced.

Results from the histologic studies of the specimens showed that all the collagen implant had the clear evidence of tissue ingrowth and new tissue production. In addition, all collagen implants did not appear to have undergone any mechanical disruption or delamination, indicating that the tissue ingrowth and incorporation would provide early stability to the implant and joint, thus obviate the need for pin fixation of the joint for up to 6 weeks as is typically done when SILASTIC or titanium implants are used in human patients. It was also of marked interest that several of the specimens appeared to be developing articular cartilage in the superficial layers of the collagen implant where the implant was adjacent to host articular cartilage. The one animal in Group 2 that had received the autogenous tendon implant showed a disorganized collagen and dense scar in the area of the implant. Such a finding would be expected at the early time point of 6 weeks.

OTHER EMBODIMENTS

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A hand augmentation device comprising a dry matrix which contains at least 75% by weight biocompatible and bioresorbable biopolymeric fibers, and has a height of 2 mm to 4 cm, a width of 0.5 cm to 6 cm, a depth of 0.5 cm to 6 cm, a density of 0.1 g/cm$^3$ to 0.5 g/cm$^3$, and a pore size of 50 μm to 300 μm.

2. The device of claim 1, wherein said biopolymeric fibers are collagen fibers or polysaccharide fibers.

3. The device of claim 2, wherein said biopolymeric fibers are collagen fibers.

4. The device of claim 2, further comprising a bioactive substance dispersed in said matrix.

5. The device of claim 4, wherein said bioactive substance is a glycosaminoglycan, a growth factor, an antibiotic, or a glycoprotein.

6. The device of claim 3, further comprising a bioactive substance dispersed in said matrix.

7. The device of claim 6, wherein said bioactive substance is a glycosaminoglycan, a growth factor, an antibiotic, or a glycoprotein.

8. The device of claim 1, further comprising a bioactive substance dispersed in said matrix.

9. The device of claim 8, wherein said bioactive substance is a glycosaminoglycan, a growth factor, an antibiotic, or a glycoprotein.

10. A hand augmentation device comprising a dry matrix which contains at least 75% by weight biocompatible and bioresorbable biopolymeric fibers, and has a height of 0.5 cm to 1.5 cm, a width of 1 cm to 2 cm, a depth of 1 cm to 2 cm, a density of 0.15 g/cm$^3$ to 0.3 g/cm$^3$, and a pore size of 100 μm to 200 μm.

11. The device of claim 10, wherein said biopolymeric fibers are collagen fibers or polysaccharide fibers.

12. The device of claim 11, wherein said biopolymeric fibers are collagen fibers.

13. The device of claim 11, further comprising a bioactive substance dispersed in said matrix.

14. The device of claim 13, wherein said bioactive substance is a glycosaminoglycan, a growth factor, an antibiotic, or a glycoprotein.

15. The device of claim 12, further comprising a bioactive substance dispersed in said matrix.

16. The device of claim 15, wherein said bioactive substance is a glycosaminoglycan, a growth factor, an antibiotic, or a glycoprotein.

17. The device of claim 10, further comprising a bioactive substance dispersed in said matrix.

18. The device of claim 17, wherein said bioactive substance is a glycosaminoglycan, a growth factor, an antibiotic, or a glycoprotein.

19. A method of fabricating a hand augmentation device of claim 1 comprising:
    obtaining biocompatible and bioresorbable biopolymeric fibers in an aqueous dispersion;
    coacervating said dispersed fibers;
    molding said coacervated fibers;
    freeze-drying said molded fibers; and
    molecularly crosslinking said dried fibers.

20. A method of using a hand augmentation device of claim 1 comprising:
    resecting diseased tissue from a bone of a hand;
    forming an implant from the device to have a size and shape substantially the same as the resected tissue; and
    securing the formed implant to the bone to replace the resected tissue.

* * * * *